United States Patent [19]

Schachter et al.

[11] 4,255,386
[45] Mar. 10, 1981

[54] METHOD AND APPARATUS FOR DESTROYING ORGANIC MATTER TO FACILITATE TRACE INORGANIC ELEMENT ANALYSIS

[75] Inventors: Myron M. Schachter, Washington, D.C.; Kenneth W. Boyer, Springfield, Va.

[73] Assignee: The United States of America as represented by the Deptartment of Health, Education and Welfare, Washington, D.C.

[21] Appl. No.: 964,969

[22] Filed: Nov. 30, 1978

[51] Int. Cl.³ .................. B01L 11/02; B01D 11/02; G01N 31/00; G01N 33/48
[52] U.S. Cl. .................. 422/101; 23/230 DC; 23/230 M; 23/230 B; 202/161; 202/169; 203/DIG. 2; 422/281; 422/282
[58] Field of Search .................. 422/101, 280–282; 202/161, 169; 203/DIG. 2, 98

[56] References Cited

U.S. PATENT DOCUMENTS 4,006,062  2/1977  Bhuchar et al. .................. 422/101 X

OTHER PUBLICATIONS

Sargent-Welch, #119 Catalog, pp. 475–477, 482, 1971.

*Primary Examiner*—Michael Marcus
*Attorney, Agent, or Firm*—John S. Roberts, Jr.

[57] ABSTRACT

The apparatus of the present invention includes a quartz flask for containing 71% nitric acid and the organic matrix to be destroyed, a Soxhlet extractor disposed above the flask, and a Friedrich coldfinger reflux condenser disposed above the extractor. A Meeker or Fisher burner is employed to provide heat to the flask and distill the acid, and the vapors are condensed within the condenser and transmitted to the extractor. An adjustable volume displacement cylinder is disposed within the extractor so as to control siphoning of the acid condensate from the extractor back into the flask. The distillation-condensation-siphoning procedure of the present invention is automatically operative once the displacement cylinder is adjusted. The organic matrix is completely destroyed so as to produce a clear, colorless acid solution within which the trace inorganic salts are disposed. The acid solution may be subsequently qualitatively and quantitatively analyzed in accordance with known techniques.

1 Claim, 1 Drawing Figure

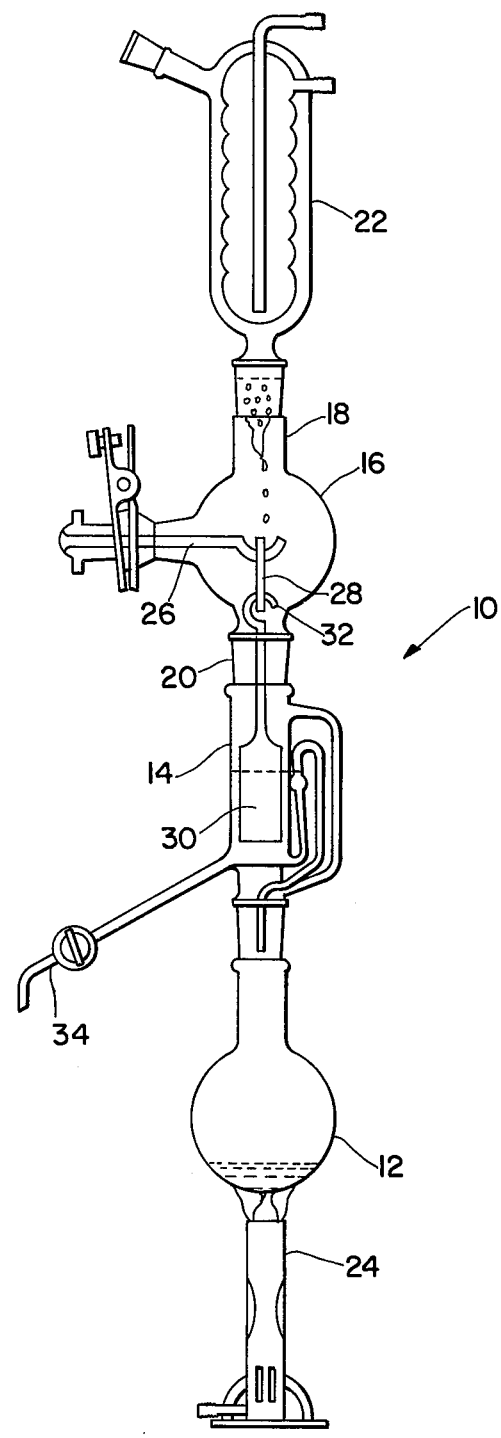

METHOD AND APPARATUS FOR DESTROYING ORGANIC MATTER TO FACILITATE TRACE INORGANIC ELEMENT ANALYSIS

FIELD OF THE INVENTION

The present invention relates generally to laboratory analytical apparatus and techniques, and more particularly to an apparatus and technique for destroying organic matter in order to facilitate trace element analysis.

BACKGROUND OF THE INVENTION

Most analytical procedures for the determination of trace elements in biological and other organic materials require that the organic matrix be completely destroyed. Both wet and dry ashing procedures are commonly used to destroy organic matrices. Dry ashing or furnace ashing is more often the chosen method simply as a matter of convenience. Problems commonly associated with dry ashing include loss of elements due to volatilization or bonding with the ashing container, the formation of ash residue which is difficult to dissolve, and the foaming of the sample. Wet ashing has been the chosen method with respect to volatile metals, such as, for example, Hg, or metals which form volatile salts when ignited in the presence of chlorides, such as, for example, As, Se, Cr, Fe, Sb, and Pb.

Furnace ignition or dry-ashing usually requires ashing acids, such as, for example, $Mg(NO_3)_2$ or $H_2SO_2$ which may introduce undesirable metal contaminants. Wet-ashing methods sometimes require catalysts, such as, for example, vanadium pentoxide ($V_2O_5$) for mercury determination, and various metal salts, including those of Cu, Ag, Au, Co, V, Ni, Pd, and Fe for Kjeldahl wet-ashing catalysts when determining nitrogen presence in organic compounds. These catalysts would also be a source of contamination or interference if the corresponding elements were being determined.

Some wet-ashing procedures are permitted to be incomplete. For example, in a digestion procedure prior to mercury determination, the fatty acids from waxes, oils, and fats are not broken down by the digestion process. Instead, they are subsequently removed by filtering the digest so as to leave the Hg salts dissolved in the aqueous filtrate. Another procedure for Hg determination brings fatty acids into solution by hydrolyzing the organic matrix with concentrated alkali. Yet another procedures uses either 50% or 30% hydrogen peroxide to produce colorless, clear digest solutions. However, these apparently completed digest solutions contain soluble organic peroxides which darken in color, and/or precipitate organic colloid micelles as soon as the peroxides decompose or are reduced. Incomplete destruction of the matrix may thus result in colloidal substances and colored products of decomposition, which would cause interferences in the determinative step of most analyses. Such interferences include clogging of atomic emission and absorption instrumentation nebulizers, formation of explosive gas mixtures during neutron irradiation for neutron activation analyses (NAA), and masking of metal chelate absorbance bands during spectrophotometric determinations.

A fusion technique using $NaNO_3$ and $KNO_3$ as a eutectic mixture oxidizes all organics including polyethylene at 390°±10° within a few minutes. Although nitrate fusion is a rapid and effective means of matrix destruction, explosion hazards associated with the use of nitrate salts to destroy organic matrices have been reported.

A widely used wet-ashing process that completely destroys organic matter uses a combination of nitric, sulfuric, and potentially explosive perchloric acids. This method is effective and safe so as long as (1) the digest is not permitted to boil dry, leading to volatilization losses and formation of possible perchlorate esters which are spontaneously explosive; (2) digestion of samples having fats and oils contents greater than 50% is not attempted; and (3) the digestion is closely watched so as to prevent charring which can also lead to volatilization losses and/or possible explosion.

OBJECTS OF THE INVENTION

Accordingly, it is an object of the present invention to provide new and improved laboratory apparatus, and a method of using the same, which will facilitate trace element analysis.

Another object of the present invention is to provide a new and improved laboratory apparatus and technique for facilitating trace element analysis which overcomes or eliminates the disadvantages noted in conjunction with the well-known conventional apparatus and techniques discussed hereinbefore.

Still another object of the present invention is to provide a new and improved laboratory apparatus and technique for facilitating trace element analysis which is quite safe to use as opposed to some of the apparatus and techniques described hereinbefore which present considerable potentially dangerous situations.

Yet another object of the present invention is to provide a new and improved laboratory apparatus and technique for facilitating trace element analysis within organic matrices which is quite rapidly operative.

Still yet another object of the present invention is to provide a new and improved laboratory apparatus and technique for facilitating trace element analysis within organic matrices which, once commenced, is automatically operative.

Yet still another object of the present invention is to provide a new and improved laboratory apparatus and technique for facilitating trace element analysis within organic matrices which eliminates or minimizes the possibilities of interference due to contaminants.

A further object of the present invention is to provide a new and improved laboratory apparatus and technique for facilitating trace element analysis within organic matrices which employs only a single acid for its operative procedure.

A still further object of the present invention is to provide a new and improved laboratory apparatus and technique which can be utilized for completely destroying all organic matter contained within an organic matrix such that trace inorganic heavy elements can be analyzed qualitatively and quantitatively by known methods without the loss of volatile elements.

A yet further object of the present invention is to provide a new and improved laboratory apparatus and technique for facilitating trace inorganic element analysis within organic matrices which minimizes expenditures for materials, labor personnel, and energy consumption.

SUMMARY OF THE INVENTION

The foregoing and other objectives are achieved in accordance with the present invention through the provision of laboratory apparatus which includes, in a vertical, serial array, a quartz flask for housing the organic matrix to be destroyed and the nitric acid ($HNO_3$), a Soxhlet extractor having a glass, volume displacement cylinder adjustably disposed therein so as to control siphoning of the condensed acid back into the flask, and a Friedrich coldfinger reflux condenser. The organic matrix and the nitric acid are initially deposited within the quartz flask, and a small amount of ammonium bromide ($NH_4Br$) may be added thereto for facilitative purposes. Heat is applied to the flask by means of a Meeker or Fisher burner, and the acid is vaporized. Condensing vapors collect within the Friedrich condenser and are held there by means of the rapidly rising vapors. When the flask becomes dry, the condensate discharges into the Soxhlet extractor so as to fill the same until siphoning occurs as determined by means of the disposition of the adjustable volume displacement cylinder. The flask will be dry during the siphoning period as a result of which the burner heats the flask and its contents to a dull red. The organic matrix is charred or carbonized, and upon the condensed siphoned acid re-contacting the red hot quartz flask, the acid flashes into superheated vapor which is substantially more reactive as an oxidizer than is the original boiling nitric acid. The carbonized matter is quickly oxidized to carbon dioxide and water, and the distillation-condensation-siphoning cycle automatically repeats itself until approximately 5% of the acid has been depleted as a result of being reduced to nitrogen and water. Adjustment of the volume displacement cylinder must then be performed in order to continue further cycling of the apparatus.

The cycling procedure is to be continued, for example, through three cycles beyond the time that the liquid in the flask becomes completely clear, and subsequently, the liquid acid is diluted and analyzed for trace inorganic heavy elements by any of several known techniques.

BRIEF DESCRIPTION OF THE DRAWINGS

Various other objects, features, and attendant advantages of the present invention will be more fully appreciated as the same becomes better understood from the following detailed description when considered in connection with the accompanying drawing wherein:

The sole FIGURE is a schematic drawing of the laboratory apparatus of the present invention for carrying out the method of the present invention.

DETAILED DESCRIPTION OF THE PREFERRED EMBODIMENT

Referring now to the drawing, the laboratory apparatus of the present invention is disclosed and generally indicated by the reference character 10. The apparatus is seen to include a 250 ml quartz flask 12 and a Soxhlet extractor 14 disposed thereabove the fluidically connected therewith. A glass bulb 16 is, in turn, disposed above extractor 14, and bulb 16 is seen to comprise upper and lower tubular conduits 18 and 20, respectively, for operatively mating with a Friedrich coldfinger condenser 22 and the Soxhlet extractor 14. The aforenoted apparatus components are thus arranged in a vertical, serial array, and a Meeker or Fisher burner 24 is disposed beneath flask 12 for heating the same as well as the contents thereof as will become more apparent hereinafter.

Bulb 16 has a suspension hook 26 adjustably and pivotably disposed therein, and a link 28 is suspended from the hooked end of hook lever 26. Both lever 26 and link 28 are fabricated of glass, and a solid glass volume displacement cylinder 30 is in turn suspended from link 28 by means of an integrally formed hooked upper portion 32. The entire suspension system enables the disposition of cylinder 30 to be selectably varied so as to positively effect siphoning of the re-cycled wet-ashing acid characteristic of the method or techique of the present invention as will become more apparent hereinafter.

In accordance with the method of the present invention, the wet-ashing acid, which is preferably nitric acid ($HNO_3$), for example, as opposed to perchloric acid or sulfuric acid due to the fact that nitric acid is safer and more easily purified, is utilized as an absorber of most of the volatile heavy trace element salts as well as an oxidizer of the organic matter and carbon present within the organic matrix. Furthermore, in accordance with the present invention, the method of the present invention comprises a wet-ashing-carbonizing in vitro technique whereby the inorganic salts from the trace metal elements contained in the organic matrix may be subsequently analyzed by known methods.

In utilizing the apparatus of the present invention for carrying out the technique of the present invention, the apparatus is set up as shown in the FIGURE, and a safety shield is recommended to be used in conjunction therewith merely as a precautionary measure against explosion. A sample of the organic matrix having a weight of not greater than 5 g (dry weight) is deposited into the quartz flask 12, an 25 ml of 71% $HNO_3$ is subsequently added to the flask 12. It is preferred that the organic matrix to be digested be essentially dry, that is, having a water content of 10% or less, for otherwise, the action of the $HNO_3$ upon the matrix is diluted. With a dry matrix, the shortest possible digestion time will be achieved. Freeze drying, vacuum drying at 40° C., or oven drying at 60° C. for samples containing greater than 10% water are acceptable methods of obtaining a dry sample in most cases.

In addition to the $HNO_3$, 0.25 g of ammonium bromide ($NH_4Br$) may also be added to the flask so as to inhibit the formation of all explosive nitrates $MNO_3$ wherein M is an alkali or alkaline earth trace metal. The nitrates, in the presence of carbon and large traces of sulfur can form explosive "black gunpowder". In addition, the $NH_4Br$ likewise inhibits the formation of explosive nitrogen trichloride ($NCl_3$). Still further, the $NH_4Br$ also serves to suppress the formation of acid insoluble oxides of chromium, iron, and aluminum which sometimes form at the charring stage of the process. The $NH_4Br$ forms $CrBr_3$ from chromium, $FeBr_3$ from iron, and $AlBr_3$ from aluminum, which are easily soluble salts and which do not decompose at temperatures above 400° C. Lastly, the $NH_4Br$ also serves to prevent the formation of the volatile compounds chromyl chloride ($CrO_2Cl_2$), $FeCl_3$, $AlCl_3$, $CuCl_2$, $ZnCl_2$, $CdCl_2$, $PbCl_2$, and $AsCl_3$. The Chromium III bromide is refractory, while the other metal bromides are much less volatile than their corresponding chlorides.

Several chips of clean quartz should also be added to the $HNO_3$ and $NH_4Br$ in order to prevent bumping during the disgestion process, and the matrix should be permitted to soak in the acid for at least 30 minutes prior to commencement of the process. Heat is then applied to the flask 12 by means of burner 24, and the acid is rapidly boiled away to dryness. Condensing vapors collect and are held within condenser 22 by means of the rising vapors, and when the flask is dry, the condensate discharges into the Soxhlet extractor 14 so as to fill the same. At this point, the disposition of glass cylinder 30 is adjusted such that siphoning of the acid condensate within extractor 14 can occur whereby the acid is able to return to the flask 12. The use of the liquid displacement cylinder 30 enables a smaller amount of acid to be employed than would otherwise be required, and the cylinder is fabricated solid so as to prevent the same from floating atop the nitric acid which has a specific gravity of 1.44.

During the period that the acid has been boiled away and until the acid condensate returns to the flask 12, the burner continues to heat the flask 12 and the matrix therein. As a result, the flask becomes dull red from the heat, and the matrix becomes charred or carbonized. In addition, upon the acid returning to the flask 12 and containing the same in its red hot state, the acid flashes into superheated vapor which is substantially more reactive as an oxidizer than is boiling nitric acid. As a result of this change of state, the matrix is quickly oxidized to carbon dioxide and water. The vapor rapidly rises within the apparatus and is again condensed, and the distillation-condensation-siphoning process automatically repeats itself within a predetermined time period until approximately 5% of the acid has been reduced to nitrogen and water thereby depleting the acid volume to the point at which the siphoning process ceases to occur. Readjustment of the cylinder 30 must then be performed, and the procedure can continue further. The process is in fact to be continued until essentially all carbonaceous and organic matter in the flask has either distilled off or been oxidized by the acid vapor and liquid. Preferably, the continuous recycling should be performed through at least three cycles beyond that period within which the liquid within the flask becomes completely clear.

Subsequent to the aforenoted cycling periods, including the periods beyond the acid clarity state, the rate of heating of the acid is reduced so as to slowly distill the same into the condenser 22 and extractor 14. At this point in the procedure, however, the acid should not be boiled away to dryness. At the point of incipient dryness, the cylinder 30 is lowered so as to siphon the acid back into the flask, and subsequently, the cylinder is raised such that during the final distillation, siphoning will not occur. The distillation is continued until only approximately 5 ml of the acid remains in the flask. At this time, the apparatus is permitted to cool to room temperature, and the acid within the extractor is tapped off through means of tap 34. The acid remaining within the flask 12 is diluted by means of hydrochloric acid so as to have a volume of 50 ml, and subsequently, the same may be analyzed for trace element contents using the Inductively Coupled Plasma (ICP) or other well-known method.

In order to determine the ability of the digestion procedure described hereinbefore to retain a large number of elements where no matrix is present, 2 ml of a standard solution of trace elements provided by the Environmental Protection Agency (EPA) was processed in accordance with the digestion technique and analyzed for comparison with the same solution not processed through the digestion procedure. The EPA solution contains 13 elements at known concentrations, and is used for quality control by EPA and other laboratories. See Table I.

In order to test the usefulness of this wet-ashing technique for destroying the sample matrix while retaining the trace elements present, 1.5 g samples of the six National Bureau of Standards (NBS) Standard Reference Materials (SRM) listed in Table II were subjected to the ashing procedure described hereinbefore. In an attempt to explain some of the lower recoveries noted when a matrix was present, 2 ml of the EPA standard solution having an added artificial matrix of 10,000 ppm each of Ca and P, and 1500 ppm each of Mg, Na, and K, was also digested and analyzed for metal content. After digestion, all of the solutions were diluted to 50 ml for analysis with the ICP. The EPA standard solution was also used to fortify a pork-and-beans sample, and a beets sample, so as to determine recoveries of added elements with a typical matrix present. Because the levels of As and Se in the EPA solution were too low to permit valid measurement by the ICP after digestion and dilution of fortified samples, two other samples, chocolate milk and freeze-dried beef kidney, were fortified with higher levels of As and Se, digested, diluted to volume, and analyzed. Cr was also added to these samples at higher levels so as to test the retention of Cr. See Table III. Finally, twelve freeze-dried total diet food composites were digested so as to determine the time requirements to destroy a wide variety of organic matrices with widely varying water contents. See Table IV.

The results of digestion of the EPA standard solution are presented in Table I, those for six NBS-SRMs in Table II, those for four food samples in Table III, and those for the total diet foot composites in Table IV. Most of the recoveries for digestion of the EPA standard solution with no matrix present were within 100%±10%. Digestion of the six NBS-SRMs gave recoveries ranging from 70%–110% for most elements. Notably low recoveries were obtained for Cr in orchard leaves and spinach, and for Fe and Mg in bovine liver. Notably high recoveries were obtained for Pb in bovine liver and spinach. However, the levels of Pb in these two samples were near the detection limit for the sample size digested.

In general, recoveries were about 10% lower for digestion of the NBS-SRMs, with a matrix present, than for the EPA standard solution with no matrix proesent. Table I shows that in the presence of the high Ca, P, Mg, Na, and K matrix, recoveries (even for Cr, Fe, and Mn) were all near 100%. With the same matrix plus high chloride (175,000 ppm), the recoveries were still close to 100%. Thus, the presence of high concentrations of elements such as Ca, Mg, and P, which might be expected to cause precipitate formation, or of chloride which could form volatile species, did not significantly affect recoveries.

Digestion of the beets sample fortified with the EPA standard solution added (Table III) gave recoveries for the added elements about the same as for the NBS-SRMs. Recoveries for elements added to the pork-and-beans sample were higher and more variable than for the beets sample. However, the pork-and-beans is more difficult to digest because of the higher fat content. Table III also shows the recoveries obtained for digestion and analysis of the chocolate milk and freeze-dried beef kidney samples fortified with As, Se, and Cr at a level of 23.9 ppm. This data shows that good recoveries are obtained for these volatile elements in the chocolate milk sample, but not for the beef kidney sample. The cause for the losses with the beef kidney sample is not known and is being investigated further.

The times required to destroy various matrices are shown in Table IV. These times are approximately one-half the time required by the HNO₃—HClO₄—H₂SO₄ procedure noted hereinbefore. This table shows as would be expected that samples with a relatively high fat content, such as, for example, meat or fats and oils, or with a relatively higher sugar content, such as, for example, sugar and adjuncts, require more time to destroy than do low fat or low sugar samples.

The initial concern when this procedure was tested in the laboratory was whether or not it was safe. During initial digestions using the uni-acid procedure of the present invention, "bumping" of the sample frequently occurred during the initial heating step. As was noted hereinbefore, however, this phenomenon can be eliminated by the inclusion of a few acid-cleaned quartz chips, for example, cut from quartz tubing, within the digestion mixture. In addition, although the flask contents sometimes burn briefly when the hot acid siphons into the red hot charred mass within the quartz flask, no explosions have occurred during digestion of several hundred samples with widely varying matrices using the procedure of the present invention. It is also noted that the particular use of the quartz flask, as opposed to a glass flask, resists thermal shock without cracking when the relatively cool nitric acid at 100° C. siphons onto the hot inner surface of the flask which has a temperature of approximately 400° C. Glass melts at 570° C., however, the same would shatter if subjected to such thermal shocks.

Thus, it may be seen that the apparatus and method of the present invention have important advantages over known prior art apparatus and methods, such as, for example, the aforenoted HNO₃—HClO₄—H₂SO₄ method, in that the present invention requires the use of only a single acid, HNO₃. Nitric acid is also much easier to purify than is either HClO₄ or H₂SO₄. For example, the nitric acid may be easily obtained by sub-boiling distillation. From the aforenoted data, it is also seen that the digestive process is substantially more rapid than previously known processes, and less energy is required to operate the apparatus. Still further, due to the automatic processing of the apparatus and method of the present invention, personnel requirements are reduced. Other apparatus and methods must be constantly monitored for explosion possibilities.

Obviously, many modifications and variations of the present invention are possible in light of the aforenoted teachings. It is to be understood therefore that within the scope of the appended claims, the present invention may be practiced otherwise than as specifically described herein.

TABLE I

| | Digested Standard Solutions | | | |
|---|---|---|---|---|
| | Concentration before digestion (ppm) | After Digestion (% Recovery) | | |
| Element | | No matrix present | Matrix A[a] | Matrix B[b] |
| Al | 3.62 | 109 | 110 | 85 |
| Be | 1.59 | 99 | 107 | 98 |
| Cd | 0.29 | 96 | 100 | 79 |
| Co | 1.58 | 98 | 106 | 96 |
| Cr | 0.84 | 93 | 108 | 94 |
| Cu | 0.41 | 96 | 85 | 100 |
| Fe | 2.71 | 101 | 110 | 103 |
| Mn | 1.59 | 101 | 105 | 101 |
| Ni | 0.61 | 100 | 105 | 95 |
| Pb | 1.41 | 92 | 103 | 96 |
| Se | 0.18 | 94 | 94 | 122 |
| V | 0.63 | 108 | 108 | 106 |
| Zn | 0.70 | 107 | 99 | 81 |
| | | 99.5 ± 5.6% | 103.1 ± 7.1% | 97.1 # 10.9% |

[a]Matrix A - aqueous acid solution plus 20,000 ppm each of Ca and P, and 1,500 ppm each of Mg, Na, and K. All elements present in same solution.
[b]Matrix B - same as Matrix A plus 175,000 ppm chloride

TABLE II

| | Digestion of NBS Standard Reference Materials | | | | | | |
|---|---|---|---|---|---|---|---|
| | NBS value in μg/g or % (% Recovery by Digestion) | | | | | | Mean |
| Element | Orchard Leaves | Bovine Liver | Spinach | Pine Needles | Wheat Flour | Rice Flour | Recovery by Element |
| Al | a | a | 870 ± 50 (93) | 545 ± 30 (83) | a | a | 88% |
| B | 33 ± 3 (91) | a | 30[a] (84) | a | a | a | 88% |
| Ca | 2.09 ± 0.03% (96) | 123[b] (101) | 135 ± 0.03% (110) | 0.41 ± 0.02% (100) | 190 ± 10 (91) | 140 ± 20 (87) | 98% |
| Cd | 0.11 ± 0.02 c | 0.27 ± 0.04 (96) | 1.5[b] (101) | <0.5[a] | 0.032 ± 0.007 c | 0.029 ± 0.004 c | 99% |
| Cr | 2.6 ± 0.2 (38) | a | 4.6 ± 0.3 (49) | 2.6 ± 0.2 (117) | a | a | 68% |
| Cu | 12 ± 1 (92) | 193 ± 10 (90) | 12 ± 2 (88) | 3.0 ± 0.3 (71) | 2.0 ± 0.3 (91) | 2.2 ± 0.3 (81) | 86% |
| Fe | 270[b,d] (85) | 270 ± 20 (64) | 550 ± 20 (86) | 200 ± 10 (79) | 18.3 ± 1.0 (89) | 8.7 ± 0.6 (92) | 83% |
| Mg | 0.62 ± 0.02% (73) | 605[b] (53) | a | a | a | a | 63% |
| Mn | 91 ± 4 (85) | 10.3 ± 1.0 (75) | 165 ± 6 (102) | 675 ± 15 (91) | 8.5 ± 0.5 (86) | 20.1 ± 0.4 (85) | 87% |
| Mo | a | 3.2[b] (109) | a | a | 0.4[b] c | 1.6[b] c | 109% |
| Ni | 1.3 ± 0.2 (83) | a | 6[b] (83) | 3.5[b] c | 0.18 c | 0.16[b] c | 83% |
| P | 0.21 ± 0.01% (100) | a | 0.55 ± 0.02% (104) | 0.12 ± 0.02% (100) | a | a | 101% |
| Pb | 44[a,d] (83) | 0.34 ± 0.08 (144) | 1.2 ± 0.2 (167) | 10.8 ± 0.5 (106) | a | a | 125% |
| Zn | 25 ± 3 (88) | 130 ± 10 (87) | 50 ± 2 (94) | a | 10.6 ± 1.0 (86) | 19.4 ± 1.0 (91) | 89% |
| Mean Recovery by | 83% | 91% | 97% | 93% | 89% | 87% | |

TABLE II-continued

Digestion of NBS Standard Reference Materials

| Element | NBS value in μg/g or % (% Recovery by Digestion) | | | | | | Mean Recovery by Element |
|---|---|---|---|---|---|---|---|
| | Orchard Leaves | Bovine Liver | Spinach | Pine Needles | Wheat Flour | Rice Flour | |
| Sample | | | | | | | |

[a] No NBS value available
[b] Unertified NBS value
[c] Not detected at sample size used
[d] In acid soluble portion

TABLE III

Digestion of Example Foods

| Element | ppm native | ppm added | % Recovery |
|---|---|---|---|
| Beets | | | |
| Al | 0.61 | 12.1 | 96 |
| Be | N.D. | 5.33 | 99 |
| Cd | N.D. | 0.98 | 94 |
| Co | N.D. | 5.30 | 91 |
| Cr | N.D. | 2.80 | 91 |
| Cu | 1.42 | 1.37 | 86 |
| Fe | 10.84 | 9.08 | 84 |
| Mn | 3.76 | 5.32 | 96 |
| Ni | 0.62 | 2.04 | 100 |
| Pb | 0.65 | 4.72 | 78 |
| V | 0.11 | 2.10 | 103 |
| Zn | 6.41 | 2.33 | 82 |
| | | | 91.7 ± 7.8 |
| Pork and Beans | | | |
| Al | 2.54 | 15.0 | 123 |
| Be | N.D. 6.60 | 101 | |
| Cd | N.D. | 1.21 | 82 |
| Co | N.D. | 6.60 | 94 |
| Cr | N.D. | 3.48 | 107 |
| Cu | 2.56 | 1.69 | 114 |
| Fe | 28.7 | 11.2 | 151 |
| Mn | 4.3 | 6.59 | 120 |
| Ni | 0.75 | 2.52 | 118 |
| Pb | 0.37 | 5.84 | 75 |
| V | 0.25 | 2.60 | 110 |
| Zn | 6.11 | 2.85 | 124 |
| | | | 106.2 ± 16.6 |
| Chocolate Mills | | | |
| As | N.D. | 23.9 | 88 |
| Se | N.D. | 23.9 | 94 |
| Cr | N.D. | 23.9 | 109 |
| | | | 97.0 ± 10.8 |
| Freeze Dried Beef Kidney | | | |
| As | .20 | 17.9 | 41 |
| Se | N.D. | 17.9 | 40 |
| Cr | .31 | 17.9 | 44 |
| | | | 41.7 ± 2.1 |

TABLE IV

Time for Sample Matrix Destruction (minutes)[a]

| Matrix | (Dry basis) | |
|---|---|---|
| | 1 gram | 5 grams |
| Dairy products I | 30 | 80 |
| Meat, poultry, fish II | 40 | 110 |
| Grain products III | 20 | 60 |
| Potato products IV | 20 | 60 |
| Leafy vegetables V | 20 | 35 |
| Legumes VI | 30 | 80 |
| Root vegetables VII | 30 | 80 |
| Garden fruits VIII | 20 | 40 |
| Fruit IX | 30 | 80 |
| Fats & oils X | 120 | 250 |
| Sugar & adjuncts XI | 60 | 115 |
| Beverages XII | 20 | 65 |
| NBS Orchard Leaves | 20 | 60 |
| NBS Bovine Liver | 40 | 110 |
| NBS Pine Needles | 20 | 60 |
| NBS Spinach | 20 | 60 |

[a] Roman numerals indicate Total Diet composite number (Thiers, "Trace Analyst," J. H. Yoe, ed., John Wiley and Sons, New York, 1957, page 637)

EXAMPLE 1

The sample of food, biological material, or organic polymer plus a small amount (0.1 gram) NH$_4$Br to prevent loss of trace chromium, tin, germanium, arsenic, selenium, and tellurium were inserted in the quartz flask. 25 ml 71% HNO$_3$ was poured into the taper joint opening at the top of the Friedrich condenser. The acid collected in the Soxhlet chamber. The adjusting lever was lowered until the cylinder displaced the acid volume to the level of incipient siphoning. A very slight further adjustment was used to siphon the acid into the quartz flask. The flask was heated strongly with a Meeker burner until the acid boiled to dryness. Condensing vapors collected and were held above the constriction at the bottom of the condenser by the rapidly rising vapors. When the flask became dry, the condensate dropped into the Soxhlet chamber filling same until siphoning occurred, returning the acid to the flask. The flask was dry for about 20 seconds, allowing the Meeker burner to heat it and its contents to dull red heat. All of the organic material in the flask was carbonized. On contacting the red hot quartz, the returning acid flashed into superheated vapor, which was many times more reactive as an oxidizer than was boiling nitric acid. The carbonized matter was quickly oxidized to CO$_2$ and water. The vapor rapidly rose to be condensed again, repeating the cycle every 1.5 to 2 minutes as long as the source of heat was continuously applied. Once set up and adjusted, this process continued automatically until after about 5% of the acid had been reduced to nitrogen and water, depleting the volume to the point where siphoning ceased to occur. Readjustment of the displacement cylinder was the only correction required, and this may be done while heating and boiling is going on.

Five cycles completely digested protein to CO$_2$ and water. Ten cycles completely degraded carbohydrate. Twenty-five cycles degraded oils, fats, and waxes. Thirty cycles degraded linear polyethylene. Four to five hours (more than 150 cycles) was required for polypropylene. Kel-F merely turned brown but was not destroyed, and Teflon was uneffected.

The size of the apparatus used permitted the digestion of 10 grams of dry material and 25 grams of wet material. The process was most rapid and most efficient when the organic matter contained less than 5% water, since water diluted the action of hot $HNO_3$ vapor.

What is claimed as new and desired to be secured by Letters Patent of the United States is:

1. Apparatus for completely destroying organic matter in order to facilitate trade inorganic element analysis, comprising:

flask means for housing acid means and an organic matrix;

means disposed beneath said flask means for heating said acid means so as to distill the same;

condenser means disposed above said flask means for condensing said distillation vapors;

means disposed between said flask means and said condenser means for controlling the return of said condensed vapors to said flask means such that said distillation-condensation cycle proceeds automatically;

said control means including means for delaying said return of said condensed vapors to said flask for a predetermined time period during which said acid within said flask is distilled to dryness, with said flask being heated to a dull red state, and with said organic matrix being charred;

said delay means comprising siphoning means interposed between said condensing means and said flask means;

said siphoning means including adjustable means being adjustable so as to properly control said return of said acid condensate to said flask means in said time-delayed manner;

said siphoning means comprising a Soxhlet extractor disposed between said flask means and said condenser means having said adjustable means disposed therein, said adjustable means comprising a volume displacement cylinder adjustably disposed within said extractor having dimensions approximating that of the inside wall of said soxhlet extractor for determining the commencement time of said siphoning of said acid condensate, said ajustable means further comprising lever and link means located within a housing means between said soxhlet extractor and said flask means, said cylinder being suspended in said soxhlet extractor by lever and link means regulating the position of the cylinder within said soxhlet extractor.

* * * * *